US 7,264,474 B2

(12) United States Patent
Sullivan et al.

(10) Patent No.: US 7,264,474 B2
(45) Date of Patent: Sep. 4, 2007

(54) PERSONALITY STYLE METHOD

(75) Inventors: Joseph R. Sullivan, Dallas, TX (US);
Frederick A. Leafgren, Stevens Point, WI (US); Lee B. Wagman, Thornhill (CA); Lorne H. Karasik, Thornhill (CA)

(73) Assignee: Personality Resources International, Ontario (CA)

( * ) Notice: Subject to any disclaimer, the term of this patent is extended or adjusted under 35 U.S.C. 154(b) by 596 days.

(21) Appl. No.: 10/245,659

(22) Filed: Sep. 18, 2002

(65) Prior Publication Data

US 2003/0036043 A1 Feb. 20, 2003

Related U.S. Application Data

(63) Continuation of application No. 09/643,035, filed on Aug. 21, 2000, now abandoned.

(51) Int. Cl.
*G09B 19/00* (2006.01)
(52) U.S. Cl. .................................... 434/236; 434/128
(58) Field of Classification Search ............... 434/236, 434/237, 238, 128, 129, 107, 109
See application file for complete search history.

(56) References Cited

U.S. PATENT DOCUMENTS

| 3,281,966 | A | * | 11/1966 | Johnson ..................... 434/238 |
| 4,682,956 | A | | 7/1987 | Krane |
| 4,714,275 | A | | 12/1987 | Engel et al. |
| 4,815,976 | A | | 3/1989 | Krane |
| 4,865,549 | A | | 9/1989 | Sonsteby |
| 4,971,561 | A | | 11/1990 | Krane |
| 5,135,399 | A | * | 8/1992 | Ryan ......................... 434/236 |

(Continued)

FOREIGN PATENT DOCUMENTS

JP 10225550 A * 8/1998

(Continued)

OTHER PUBLICATIONS

Translation of JP-10225550 to Yoshiki et al.*

(Continued)

*Primary Examiner*—Dmitry Suhol
(74) *Attorney, Agent, or Firm*—Robert Platt Bell; Steve Shaw

(57) ABSTRACT

In accordance with an embodiment of the present invention, there is provided a plurality of color-coded cards and representing four personality styles and a set of two cards representing the Extraversion-Introversion scale of Carl Jung. On each set of two (2) cards, there is one that lists twenty (20) characteristics of the particular style associated with that card on a plurality of removable strips. The other card in the set of two (2) has a blank side to place the removable strips that characterize each participant. On the reverse side of this card is printed the workplace environment that most appeals to a person of this particular style. Each card has a place for a simple score, (i.e. a simple sum of the characteristics chosen). The color-coded cards are ordered numerically. The Extravert-Introvert (E-I) card is also scored. Participants are asked to place color-coded dots representing each participant's particular order of styles on their nametags. The first style represents a participant's dominant personality style. The combination of all four styles with the Extraversion-Introversion components represents the participant's personality temperament or profile.

14 Claims, 20 Drawing Sheets

U.S. PATENT DOCUMENTS

| | | |
|---|---|---|
| 5,269,691 A | 12/1993 | Waldman |
| 5,282,631 A | 2/1994 | Baker |
| 5,372,509 A | 12/1994 | Brocato et al. |
| 5,421,765 A | 6/1995 | Lehmann et al. |
| 5,441,262 A | 8/1995 | Figone et al. |
| 5,692,750 A | 12/1997 | Poole |
| 5,702,253 A | 12/1997 | Bryce et al. |
| 5,795,155 A * | 8/1998 | Morrel-Samuels .......... 434/107 |
| 6,056,549 A * | 5/2000 | Fletcher ...................... 434/112 |
| 6,109,925 A | 8/2000 | Druckman et al. |
| 6,159,015 A * | 12/2000 | Buffington et al. ......... 434/236 |

FOREIGN PATENT DOCUMENTS

WO    WO89/09697    10/1989

OTHER PUBLICATIONS

Birkman, Roger, PhD., "True Colors" © 1995, Thomas Nelson, Inc., Nashville, TN, ISBN 0-785207856-7.

* cited by examiner

5

- Action oriented
- Adventuresome
- Likes challenges
- Gets immediate results
- Competitive
- Like variety
- Needs freedom
- Able to act in a crisis
- Great negotiator
- Decisive and quick to act
- Quick-witted and humorous
- Likes tangible rewards
- Risk-taker
- high need for motility
- Takes initiative
- Seeks high visibility
- Direct communicator
- Non-judgmental
- Spontaneous
- Appears confident

13

(c) 2000 Personality Resources International

Workplace Environment

"I am most comfortable in a workplace that is unstructured and challenging. I like movement and high energy. I need freedom to move ahead and get things done. I like to make things happen. I can spot problems as they arise. I am good at negotiating agreements or plans of action."

The Ideal *Action Way* (Orange) environment:

33

- action oriented
- *new and varied activities*
- provides power and authority
- provides prestige and challenge
- opportunities for individual accomplishments
- wide scope of operations
- gives direct answers
- opportunity for advancement
- freedom from controls and supervision
- unstructured and flexible
- exciting and dynamic Strengths *Action Way* (Oranges) *bring to the work environment:*

35

- immediate response to problems
- run organization to meet current needs
- handle crisis situations
- see what's negotiable
- ingenious and resourceful
- direct and straightforward
- know how to expedite things
- a practical approach to concrete problems
- willing to take risks
- looks at the world and see facts and realities
- ability to do a variety of tasks simultaneously with ease
- sense of urgency when situation demands it © 2000   Personality Resources International   (800) 661-2636
         Dallas, TX        (972) 247-8988
         Toronto, ON       (905) 709-9019
         Text from: *The Corporate Communications Guide*

Figure 3C

30 — Workplace Environment

"I am most comfortable at a worksite that is structured, giving me a sense of efficiency and permanence. I like worksites where my space is well defined. Worksites with large clocks, bulletin boards with schedules, and specified rewards for accomplishment raise my confidence and performance level. I look forward to work where my supervisor rewards colleagues."

The ideal <u>Organized Way</u> (Gold) environment:

33 —
- ordered
- permanent
- efficient
- collaborative
- secure and safe
- maintenance of status quo
- predictable routines
- credit for work accomplished
- sincere appreciation
- identification with a group
- standard operating procedures
- minimal conflict

Strengths <u>The Organized Way</u> (Golds) bring to the work environment:

35 —
- good at time management
- realistic
- practical
- decisive
- follow rules, policies, and procedures
- bring a planned, organized approach to the task
- dependable for follow through
- thorough and precise, especially with detail
- focus on what needs to be done
- establish policies, rules, schedules © 2000  Personality Resources International  (880) 661-2636
Dallas, TX  (972) 247-8988
Toronto, ON  (905) 709-9019
Text from: *The Corporate Communications Guide*

Figure 4C

Workplace Environment

30

"I am most comfortable in a work environment which is unstructured and creative. I like to sit by myself and think without noise or intrusion. I also like working with co-workers that model highly creative successful endeavors done by teams of scientists, engineers, and technicians working together."

The Ideal _Logical_ Way (Green) environment:

33

- unstructured
- high-tech and scientific
- challenging and innovative
- flexible as to time and organization
- permit independent work
- involve problem solving, exploration, and innovation
- permits debate and discussion
- provides clearly defined performance expectations
- values quality and accuracy
- opportunities to demonstrate expertise
- control over those factors that affect their performance
- recognition for specific skills and accomplishments Strengths _Logical Way_ (Greens) bring to the work environment:

35

- focus on mission of organization
- build conceptual frameworks or systems
- look at the world and see possibilities, meanings and relationships
- examine consequences analytically and impersonally
- architects of change
- conceptualizing and designing especially with regard to organizational change
- set high standards
- can see the core of complex issues or problems
- see the larger picture
- are challenged most when someone says it can't be done © 2000   Personality Resources International   (800) 661-2636
        Dallas, TX   (972) 247-8988
        Toronto, ON   (905) 709-9019
        Text from: _The Corporate Communications Guide_

- Relates well with others
- Expresses feelings
- Sincere and authentic
- People-oriented
- Expresses appreciation and approval
- Values self-discovery
- Cooperates well with others
- Maintains high integrity
- Values personal relationships
- Good group and team participant
- Growth oriented
- Inspirational
- Empathic
- Seeks harmony
- Encourages others
- Sensitive to others' needs
- Trusting
- Adaptable
- Compassionate
- Influencing (c) 2000 Personality Resources International

Figure 6A

Workplace Environment

30

"I am most comfortable in a work environment that allows for personal interaction, individual creativity and expression. Worksites centered in discussion where supervisors and employees work together and share decision-making. Build my self-confidence, giving me a chance to grow and work alongside other employees with whom I will form long-lasting relationships."

**The ideal *Relationship Way* (Blue) environment:**

33
- interactive
- personal
- friendly and social
- relaxed and unstructured
- freedom of expression
- democratic relationships
- freedom from control and detail
- opportunity to verbalize proposals
- opportunity for social recognition

**Strengths *Relationship Way* (Blues) *bring to the work environment:***

35
- they are sensitive to the needs of people
- give people all the time they need
- see possibilities, meaning, and relationships
- effective in getting people to work together
- draw out the best in people
- sensitive to organizational climate
- work with and through people
- communicate organizational norms
- insightful and charismatic
- they are understanding and compassionate © 2000  Personality Resources International  (800) 661-2636
Dallas, TX  (972) 247-8988
Toronto, ON  (905) 709-9019
Text from: *The Corporate Communications Guide*

Figure 6C

Extraversion vs. Introversion

Extraverts pr fer:

73

* to process their understanding of the world externally
* to draw energy from outside, from the external world of people activites and things
* to verbalize observations, data, ideas, thoughts and beliefs in dialogue with others and to be actively involved with them
* action
* involvement and interaction, which energizes them
* opportunities for participation and involvement with others
* to be "up front" with what they are thinking or feeling It is usually easy to know what extraverts are thinking or feeling - they tell you! For approximately seventy-five percent of the population, extraversion is the preferred way of communicating and relating.

Introverts prefer:

75

* to process their understanding of the world internally
* to draw energy from their inner world of ideas, emotions and impressions
* to process observations, data, ideas, thoughts and beliefs internally
* not to engage in constant dialogue with others but will share their ideas if asked
* to focus on their own worlds of concepts and ideas
* private time to re-establish lost energy, because they will lose energy through constant interaction
* to be more private about personal matters Introverts can be very sociable, but may reveal less information about themselves than extraverts. Approximately twenty-five percent of the population prefers introversion.

According to Jung, the division between introverts and extraverts is the most important distinction between people because it describes the source, direction and focus for one's energy. A lack of understanding between these two orientations can lead to serious-interpersonal difficulties.

Copyright 2000    Personality Resources International    All Rights Reserved

Profiling Your Personality

Directions:

1) Remove the 5 Personality Style Cards and the Personal Characteristic Sheets from the pocket of this book.
2) Identify the characteristics on each sheet that describe your personality style. Remove the characteristic strips from the personal characteristics sheet and place them on the appropriate personality style characteristics card, (blue strips on the blue personality characteristics card, green on green, etc. For the extraversion or introversion characteristics place the white behavior characteristics on the white section of the characteristics card and black behavior characteristics on the black section of the characteristics card.

810

3) Order your four Personality Style cards in descending order from the card with the most characteristics to the card with the least characteristics. This probably indicates your personality style profile. If you believe that this is not accurate, reorder the cards in the sequence that you believe best reflects your personality style profile.
4) Once you have determined your preferred personality style, including your extraversion and introversion preferences card, place dots in the appropriate order in the circles below.

Scores

 Extraversion (White)
OR
Introversion (Shaded)

 Primary Personality Style:

820

 Second Personality Style:

830

 Third Personality Style:

 Fourth/Last Personality Style:

5) Place a set of the Personality Style dots on your nametag (in the order that you selected).

6) *Please Remember:*
We have within us all four-personality styles. The order of our preference is a significant determinant of how we function in our lives.

Copyright 2000 © Personality Resources International v.1
Phone: 905-709-9019 Fax: 905-709-9605 E-mail: info@personalityresources.com

Figure 8

PERSONALITY STYLE METHOD

CROSS-REFERENCE TO RELATED APPLICATIONS

The present application is a Continuation Application of U.S. patent application Ser. No. 09/643,035 filed Aug. 21, 2000, entitled "PERSONALITY STYLE APPARAUS AND METHOD OF USING SAME", incorporated herein by reference now abandoned.

FIELD OF THE INVENTION

This invention relates to the field of psychological testing, more particularly the invention relates to identification of personality styles employing cards with selectable peel-off stickers and business methods to provide for interpersonal communications and human relationship management.

BACKGROUND OF THE INVENTION

As the global economy and the demands of technological sophistication continue to change the workplace it becomes increasingly more important to understand, appreciate and better communicate with co-workers and other employees or managers. The management of human relationships and the appreciation of relating one's personality style to another is crucial to success in business, as well as in the management of all personal and professional relationships, today. There is a need to create and foster an environment that results in greater productivity and increased positive morale for everyone in an organization. There is also a need for improved relationships with external clients and customers. Hopefully, increased employee satisfaction leads to increased customer satisfaction.

There are various testing methods to provide analysis of personality and behavior. Life Styles Inventory (LSI1) by Human Synergistics® (Plymouth, Mich.) identifies 12 behaviors or styles. After a series of questions are answered and tabulated, the results are graphed into polar coordinate sheet called a LSI circumplex. This requires testing in advance and waiting for results to be tallied and the graph to be prepared. This can't be done in real-time such as in a team building meeting. Additionally, these tests are forced choice, which potentially eliminates certain sets of personality temperaments.

The Taylor-Johnson Temperament Analysis Profile is another tool for personality identification. The subject is required to answer a battery of questions. The questions are tallied and graphed on a line graph. The graph has traits on the x axis. The y axis illustrates the percentage of which the person tested illustrates that trait. 100 percent indicating the trait and zero percent indicating the trait opposite. Again, advance testing is required before any team-building exercise or interpretation can take place.

The Benziger Thinking Styles Assessment (BTSA) helps identify the mode of thinking most productive for the person tested. The BTSA identify Extroversion and Interversion following the work of Dr. Carl Jung.

As early as 1923, Dr. Carl Jung, considered the founder of contemporary psychological type and temperament, set the foundation for classifying personality and behavior styles in his book *Psychological Type* (Harcourt & Brace, 1923). Jung's work developed those theories of differing systems and analyses into what is known today as personality type and temperament. Jung had come to believe that all people are different in fundamental ways although they all have the same multitude of instincts driving them from within. What seemed to be most important, he said were the psychological preferences for how we function. Dr. Jung also developed the theory of Shadow Energy. Psychologists, Kretschner and Spranger, contemporaries of Jung, also attempted to classify personality types, but neither made the impact of Carl Jung. In his research Jung also studied the ancients from the East and the West. He used the writings of Hippocrates and Plato and others to begin his study.

As Jung believed, extraverts prefer to process their understanding of the world externally. They draw energy from outside, from the external world of people, activities and things. Introverts prefer to process their understanding of the world internally. They prefer to draw energy from their inner world of ideas, emotions, and impressions.

Shadow energy, Jung taught, is the negative and/or hidden or rejected side of personality. Everyone has a shadow. If we fail to recognize our shadow it may, as Jung suggested, control us and may show up in our lives in the form of addictions, compulsions or other destructive behaviors.

Following Jung's work, Isabel Briggs-Myers and David Keirsey have greatly contributed to the understanding of the psychology of personality.

Isabel Briggs-Myers, along with her mother, Katherine Briggs, following the Jungian psychological concepts, developed the Myers-Briggs Type Indicator (MBTI), a forced choice instrument. The Myers-Briggs system classifies personality into sixteen different types. It is widely used in many environments today, from within the corporate climate to educational institutions and by professionals engaged in counseling, education, consulting and/or training.

David Keirsey developed The Keirsey Temperament Model—utilizing the four personality temperaments: the Artisan, the Guardian, the Idealist and the Rational. Keirsey's work is widely known and popularized through, *Please Understand Me, Please Understand me II*, and *Portraits of Temperament*. (www.keirsey.com).

Don Lowry, a student of Keirsey, then used the temperament model to develop a system called True Colors® Communications Group (Bermuda Dunes, Calif.). Lowry's system uses four colors—Blue, Green, Orange and Gold, to designate personality types and behavior styles. Dr. Roger W. Birkman also developed a system, in 1951, which used colors as a metaphor for Carl Jung's four personality types. Dr. Birkman's system is described in his book *True Colors*, (www.birkman.com)

The MBTI, Benziger Thinking Styles Assessment (BSTA) (www.beziger.org), Taylor-Johnson Temperament Analysis, and the Herman Brain Dominance Instrument are well known in the personality testing field in which specific groupings of characteristics are identified with four basic personality styles.

These models led to development of personality testing to help an individual to determine a proper vocation or to further understand his or her own motivations or feelings. Testing and use of the results have been increasingly used in the business world.

Determining and identifying personality types and temperament per the above models normally involves providing an individual with a battery of tests having the individual answer a series of questions relative to certain broad categories of activities, emotions, motivations or goals. The individual's responses are then correlated and a general personality pattern is identified, and placed in presentation form for counseling, team building and other such activities. Most of the models reported above use a forced choice questionnaire that eliminates, for some individuals, an accurate profiling of their personality. In these models the tabulation process is extremely onerous and time-consuming, and may lead to loss of motivation by the subject. This form of assessment increases anxiety for many individuals.

Furthermore, access to such a battery of tests presents a personal security problem. For example, the detailed answers provided by an individual in an employment environment might provide fellow employees or the employer itself with information needed to manipulate the individual. The detail answers may provide information on the individual's fears and concerns and on what "hot buttons" to use to control the individuals behavior.

Therefore, the need arises for an apparatus and method to provide an easy "user-friendly" real-time personality testing, evaluation and presentation that is also secure from abuse.

SUMMARY OF THE INVENTION

The present invention provides a method and apparatus that facilitates growth and enhancement of human skills. Such human skills develop increased self-awareness, increased awareness of others, and effective communication and relationship skills enabling people to work together effectively toward common goals.

Briefly, a preferred embodiment of the present invention includes a plurality of cards. Preferably, eight cards are color-coded and represent four personality styles. The final two cards represent the Extraversion-Introversion scale of Carl Jung. On each set of two (2) cards, there is one that lists twenty (20) characteristics of the particular style associated with that card on a plurality of removable strips. The other card in the set of two (2) has a blank side to place the removable strips that characterize each participant. On the reverse side of this card is printed the workplace environment that most appeals to a person of this particular style. Each card has a place for a simple score, (i.e., a simple sum of the characteristics chosen). The color-coded cards are ordered numerically. The Extravert-Introvert (E-I) card is also scored. Participants are asked to place color-coded dots representing each participant's particular order of styles on their nametags. The first style represents a participant's dominate personality style. The combination of all four styles (colors) with the Extraversion-Introversion components represents the participant's personality temperament or profile.

The features and advantages of the invention will be apparent from the following detailed description of the preferred embodiments.

BRIEF DESCRIPTION OF THE DRAWINGS

FIG. 3A is an illustration of "The Action Way" or Orange strip-sticker card.

FIG. 3C is an illustration of the reverse side of "The Action Way" or Orange strip-sticker application card shown in FIG. 3B.

FIG. 4C is an illustration of the reverse side of "The Organized Way" or Gold strip-sticker application card shown in FIG. 4B.

FIG. 5C is an illustration of the reverse side of "The Logical Way" or Green strip-sticker application card shown in FIG. 5B.

FIG. 6A is an illustration of "The Relationship Way" or Blue strip-sticker card.

FIG. 6C is an illustration of the reverse side of "The Relationship Way" or Blue strip-sticker application card shown in FIG. 6B.

FIG. 7C is an illustration of the reverse side of the Extraversion vs. Introversion strip-sticker application card shown in FIG. 7B.

FIG. 8 is an illustration of a worksheet that illustrates instructions for the use of the present invention creating a profile of the participate's personality.

DETAILED DESCRIPTION OF THE PREFERRED EMBODIMENTS

Figure 1:
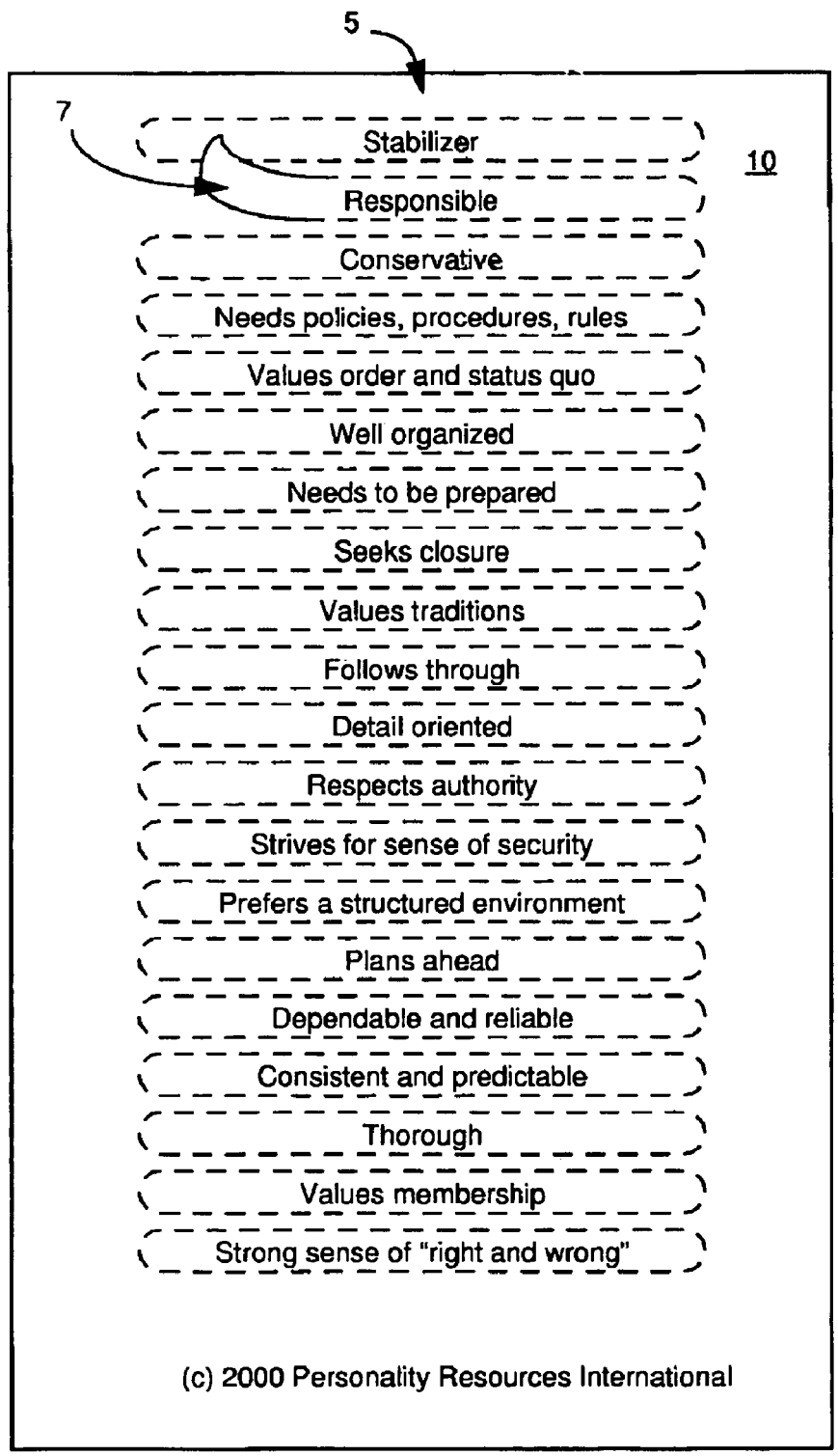
FIG. 1 is an illustration of a card of peel-off strip-stickers in accordance with one embodiment of the present invention.

FIG. 1 is an illustration of a peel-off strip-sticker card in accordance with the invention. Peel-off sticker card 10 may preferably be fabricated from two layers of materials. A base layer may be fabricated from paper with a wax coating on a first side. A second layer may be fabricated from a clear flexible plastic or vinyl film with an adhesive coating applied to a first side and printed material applied to a second side. The second layer may form a peel-off sticker layer.

The layered sheet may be produced as a large single sheet or as a roll of the material. The sheet or roll is then sent to the printer. The printer applies printer's ink on the side that has the vinyl film to form desired printed material. The sheet may be kiss-cut to form individual peel-off labels 15, each containing a personality characteristic or trait 5. The sheet may then be die-cut to form the individual cards such as 10. Alternatively, the cards 10 may be provided to the printer in the final size and already kiss-cut. The use of the term printer is intended to include non-professional printing process, which may include but is not limited to desktop printing.

Peel-off sticker card 10 may comprise a plurality of personality characteristics or traits 5 in the form of a word or a phrase. There may be any number of personality characteristics listed on a card. However, for the tally described herein to function, the number of characteristics on each card must be the same. In the preferred embodiment of the invention, each card presents twenty (20) characteristics. Each trait 5 may be printed on the card with a kiss cut around the printed trait word or phrase in order that material comprising the word or phrase may be lifted from the card applied to a second card, which will be described below.

Reference number 15 illustrates the material comprising an individual trait being lifted from the surface of the second layer of the card material. The words or phrases form a set of traits related to a personality style. The traits 5 of card 10 are related to the style or way referred to as "The Organized Way."

The card may be printed with background colors or designs. The color may be a design related to a certain company colors, (or the color may be related to a color related to a certain personality style). In the example of FIG. 1, the style related to the set of traits identified with the color of Gold. Designs may also be printed to reflect the personality style. For example, for the card shown in FIG. 1, designs expressing organization may be printed as background design.

Figure 2A:
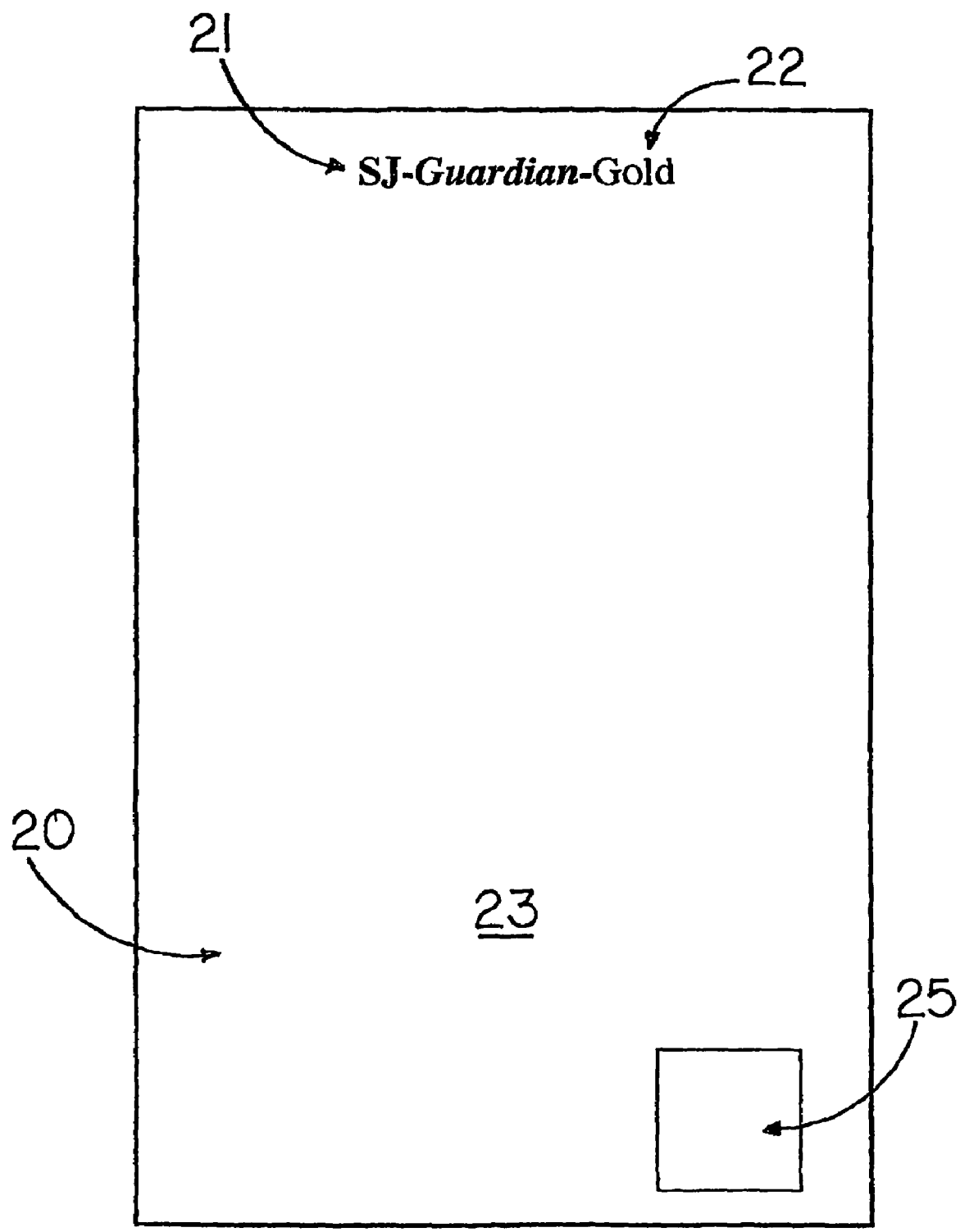
FIG. 2A illustrates a sticker application card in accordance with the invention.

FIG. 2A illustrates a sticker application card in accordance with the invention. The sticker application card may be fabricated of heavy card stock. The card has a first side and a second side. The first side of sticker application card 23 comprises an area 20 on which to apply peel-off stickers from a peel-off sticker card such as that shown in 10, an area in which to enter a count of the number of stickers applied to the card 25. Identification of the personality style is provided for at 21 and 22. In the example, this card is for a Gold 22 personality style. This may also be described as "The Organized Way" 21. The second side of card comprises text that describes the personality style and elements of that style. An example is the workplace environment and the strengths that the individual with this style brings to the work environment.

In a method to use the cards to determine personality styles, an individual may be tested by a tester or may self-test. The individual selects words or phrases with which the individual identifies and feels that applies to them. After the individual applies stickers of all the characteristics with which they identify a count of the number of stickers may be obtained and may be written in area 25.

Figure 2B:
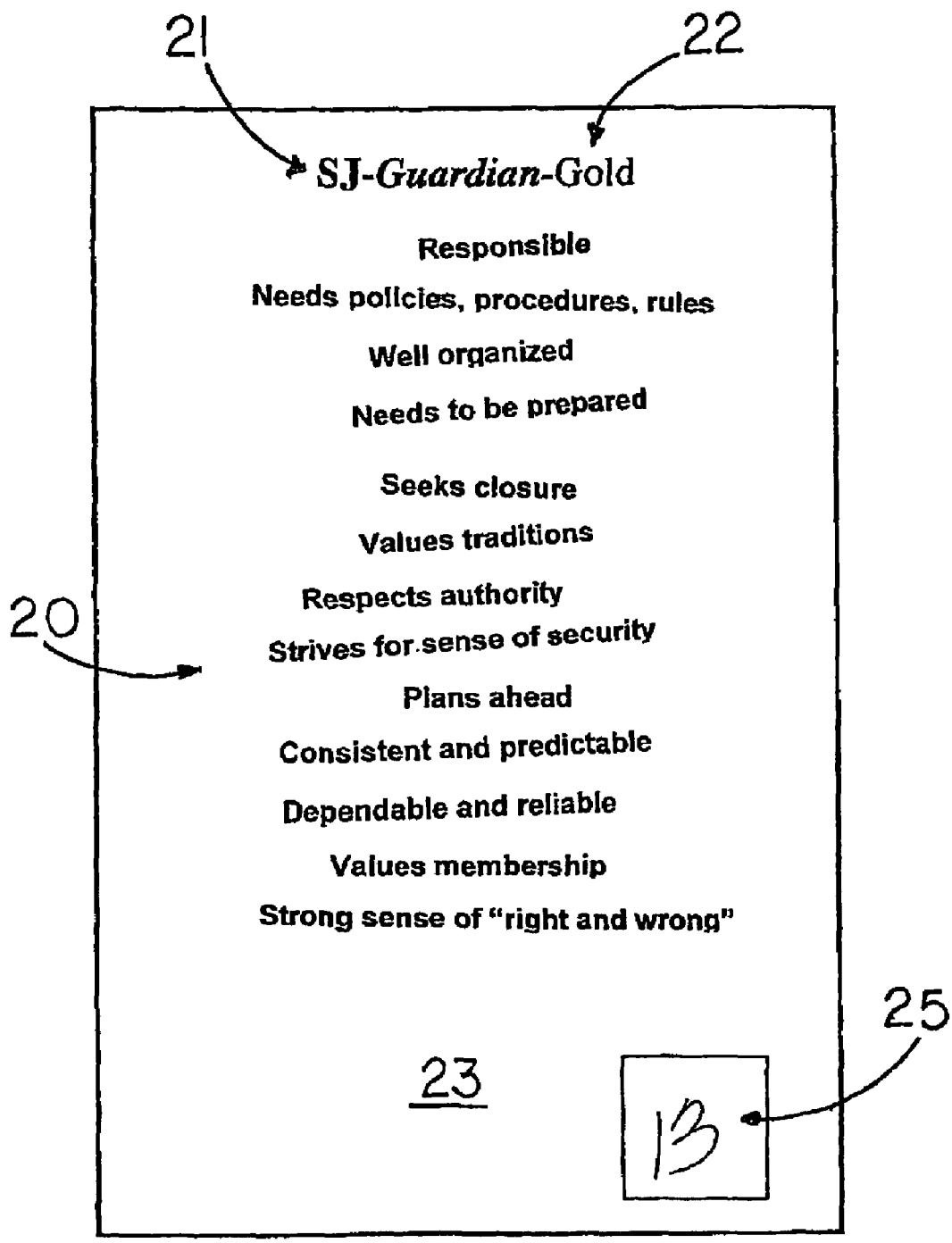
FIG. 2B illustrates an example of selected stickers from the strip-sticker card shown in FIG. 1 applied to the sticker application card shown in FIG. 2A.

FIG. 2B illustrates the sticker application card 23 of FIG. 2A with stickers selected by an individual and applied to area 20. In this example, 13 of the 20 stickers with characteristics 5 have been applied to sticker application area 20 of sticker application card 23; this count has been entered in count information area 25.

The steps described above are repeated for each of the remaining cards. The card with the highest count is the primary personality style of the individual, the second highest is the secondary personality style of the individual, and so on.

The cards may be completed in any order. Therefore, although the cards are described in a particular color order, they may be completed in other orderings or even simultaneously.

The cards may be used in association with a descriptive manual and a handbook. An example, is *Corporate Communications Guide and Communication & Relationship Interactive Handbook*; Fred Leafgren and Joseph R. Sullivan; Personality Resources International; (Dallas, Tex.; Chicago, Ill. and Richman Hill, Ontario, Canada; www.personalityresources.com). Both guide and handbook are filed herein as Appendix A and Appendix B respectively and incorporated herein by reference.

Figure 3B:
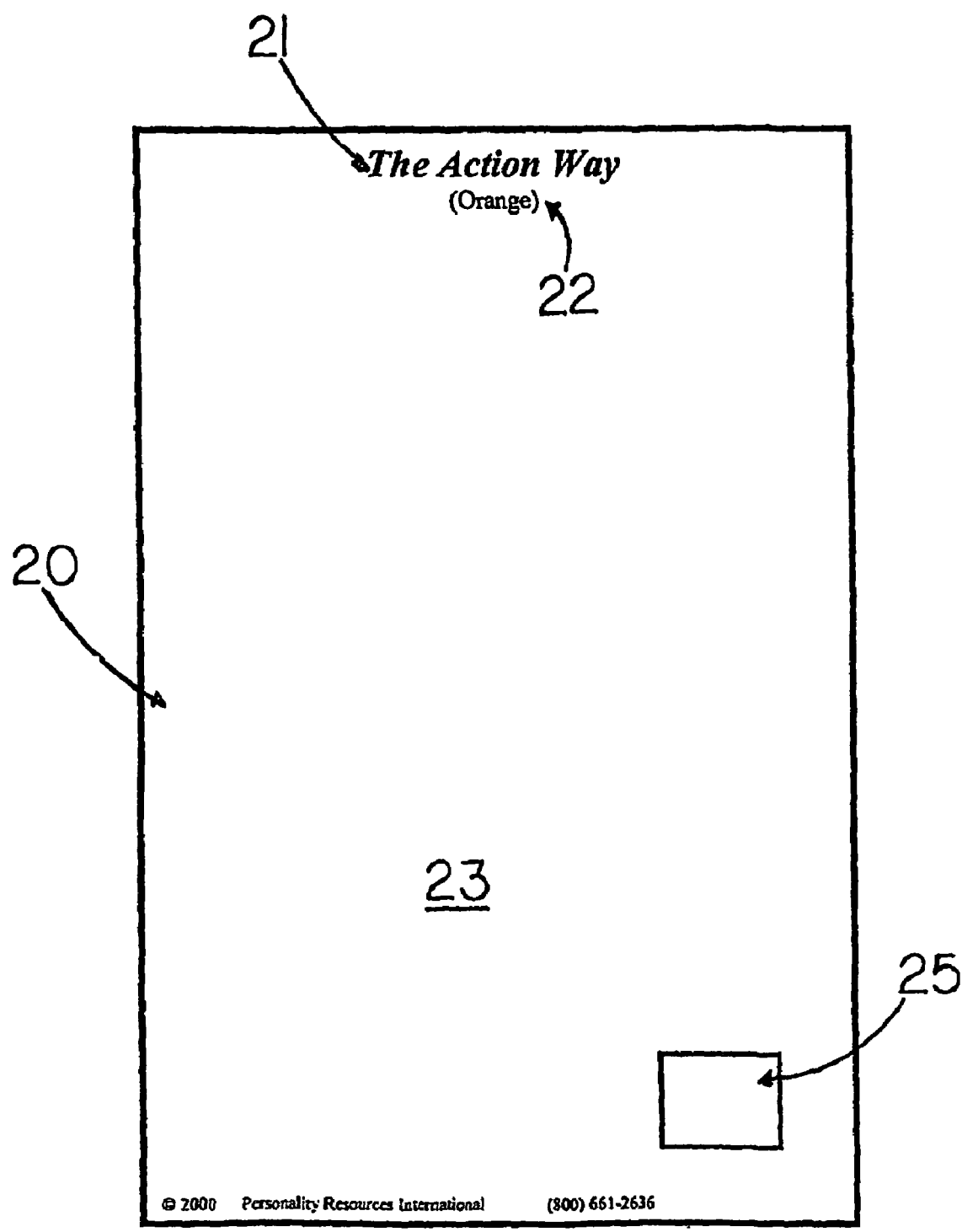
FIG. 3B is an illustration of "The Action Way" or Orange strip-sticker application card.

FIG. 3A illustrates the list of characteristics on the first peel-off sticker card, which is the Orange card 13 with its list of characteristics 5. The individual selects the characteristics 5 with which the individual identifies and applies them to the sticker application area 20 of card 23 of FIG. 3B. The stickers applied are counted and entered in area 25. Indicia 21 and 22 identify the card as belonging to the Orange category 22 and the personality style as "The Action Way." The reverse or second side of the sticker application card comprises information regarding the individual with this style, relative to preferred work environments.

FIG. 3C is an exemplar of information, which may be used to facilitate the use of the card. Quote area 30 illustrates an example of what the individual who identifies as Orange, "The Action Way," would feel about the workplace environment. An ideal environment description 33 describes the ideal work environment for the individual who identifies with "The Action Way" personality style. Strength area 35 illustrates the strengths that the individual who identifies with "The Action Way" personality style brings to the workplace environment.

Figure 4A:
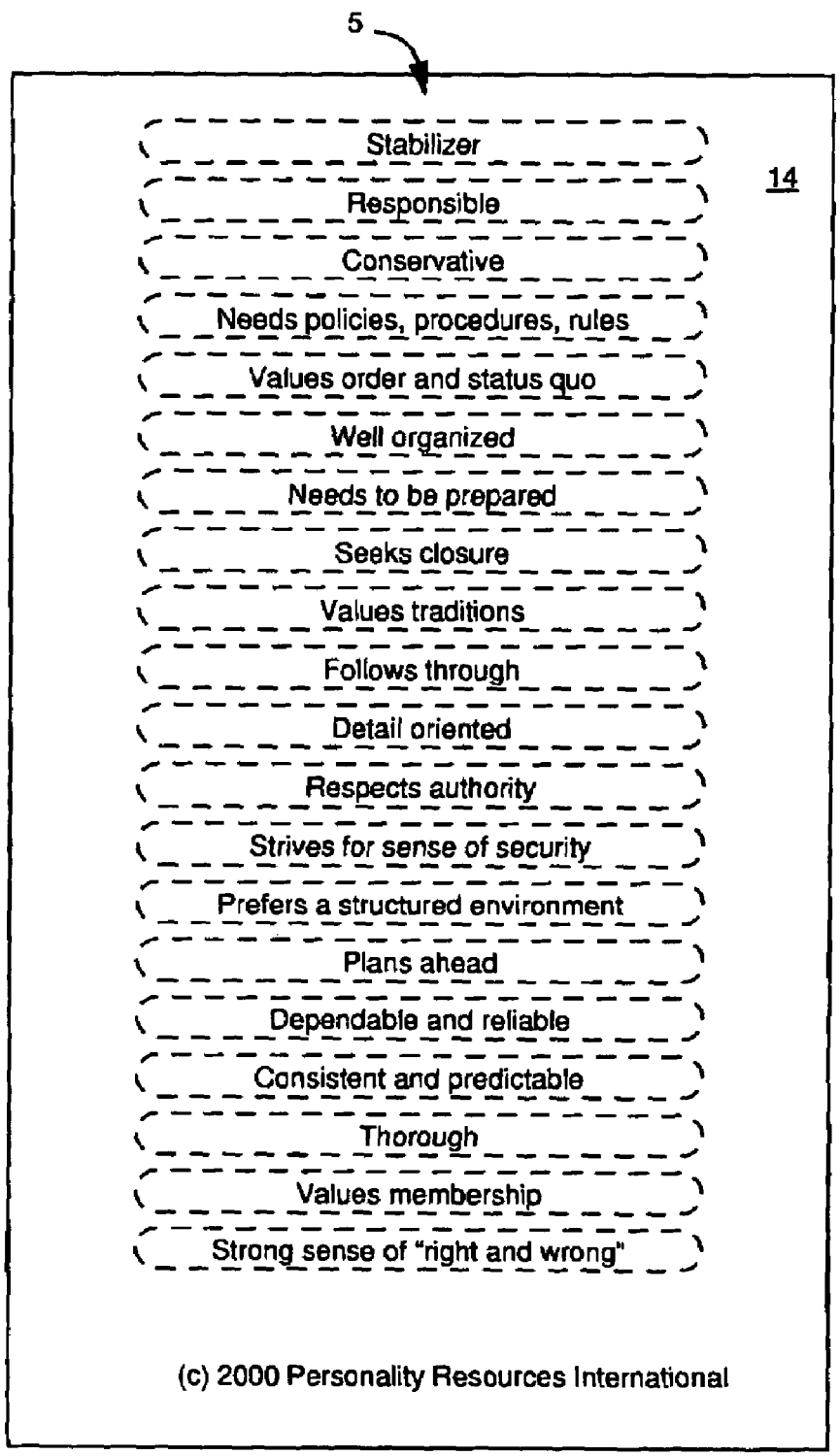
FIG. 4A is an illustration of "The Organized Way" or Gold strip-sticker card.
Figure 4B:
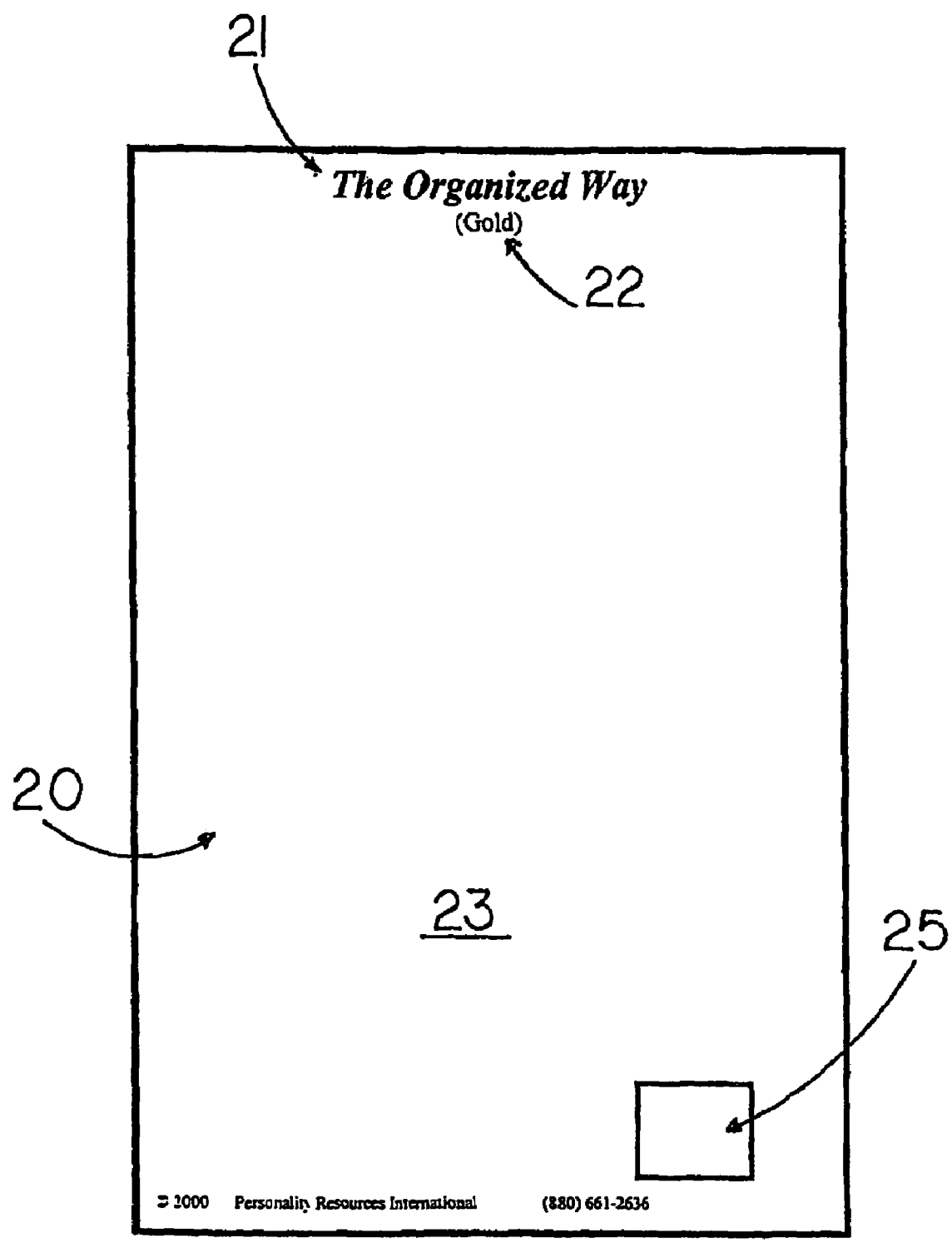
FIG. 4B is an illustration of "The Organized Way or Gold strip-sticker application card.

FIG. 4A illustrates the list of characteristics on the first peel-off sticker card that is the Gold, "The Organized Way," card 14 with its list of characteristics 5. The individual selects the characteristics 5 with which the individual identifies and applies them to the sticker application area 20 of card 23 of FIG. 4B. The stickers applied are counted and entered in area 25. Indicia 21 and 22 identify the card as belonging to the Gold category 22 and the personality style as the "The Organized Way." The reverse or second side of the sticker application card comprises information regarding the individual with this style.

FIG. 4C is an exemplar of information, which may be used to facilitate the use of the card. Quote area 30 illustrates an example of what the individual who identifies as Gold, "The Organized Way," would feel about the workplace environment. An ideal environment description 33, describes the ideal work environment for the individual who identifies with the "The Organized Way" personality style. Strength area 35 illustrates the strengths that the individual who identifies with the "The Organized Way" personality style brings to the workplace environment.

Figure 5A:
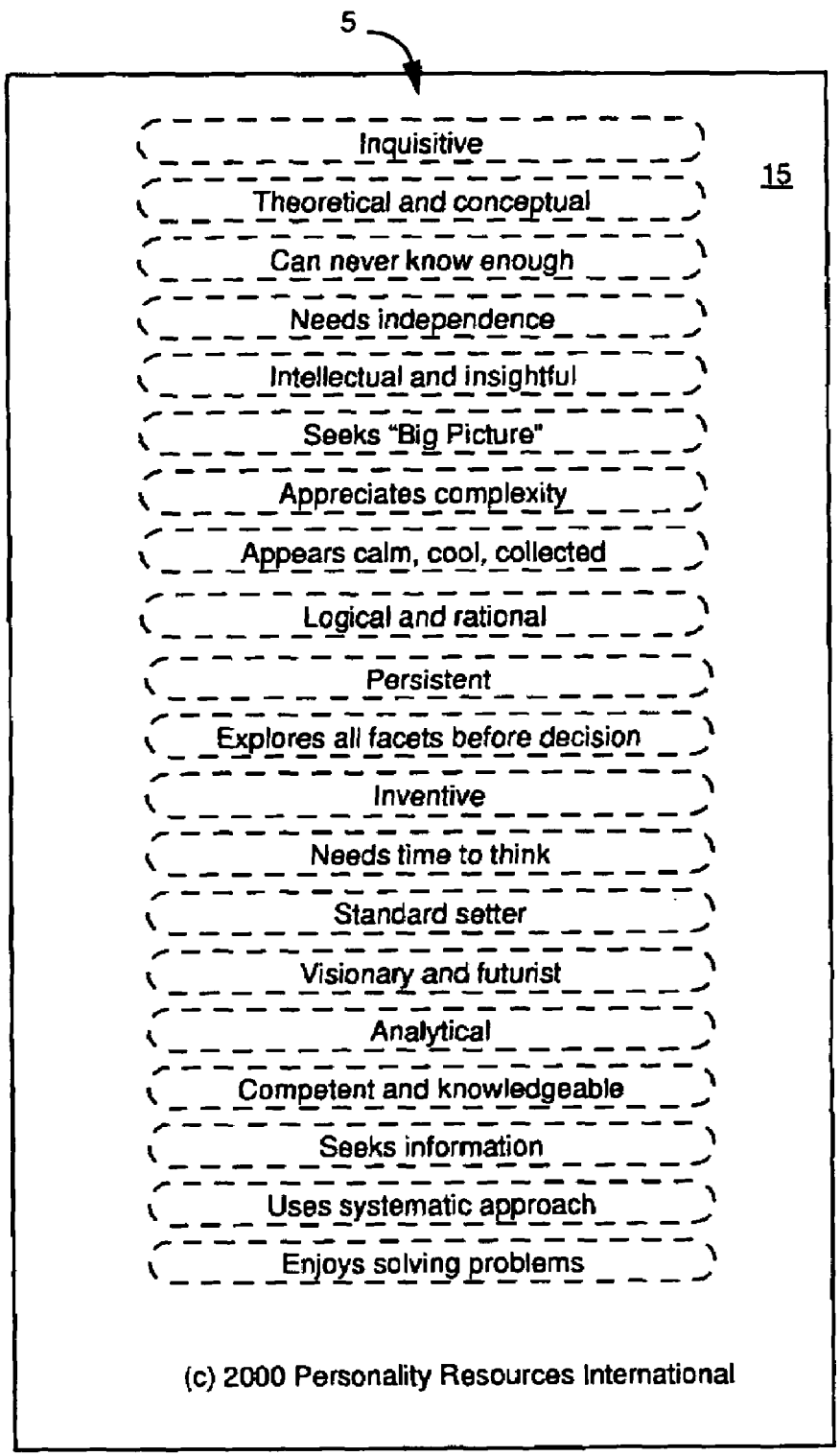
FIG. 5A is an illustration of "The Logical Way" or Green strip-sticker card.
Figure 5B:
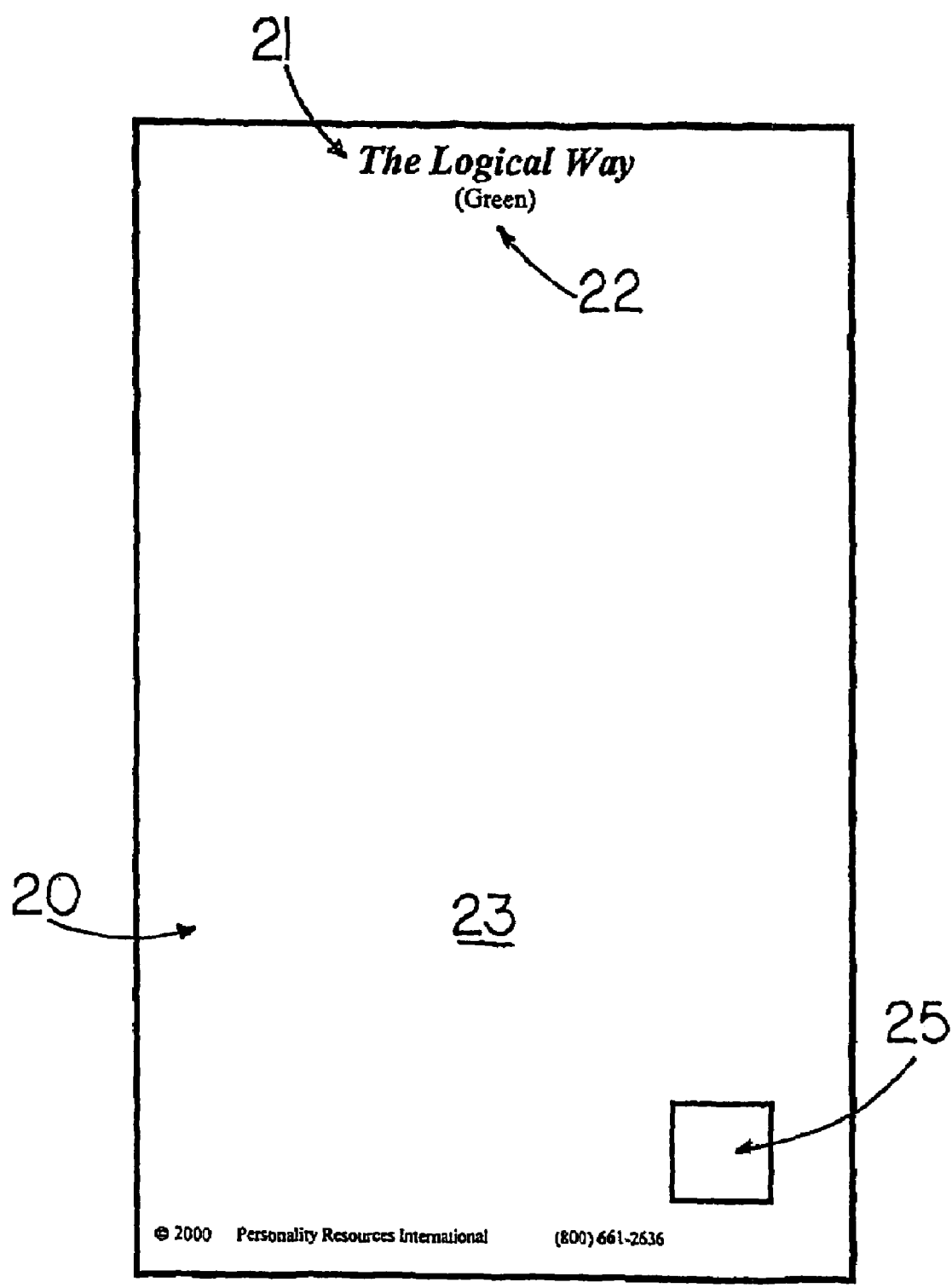
FIG. 5B is an illustration of "The Logical Way" or Green strip-sticker application card.

FIG. 5A illustrates the list of characteristics on the first peel-off sticker card that is the Green, "The Logical Way," card 15 with its list of characteristics 5. The individual selects the characteristics 5 with which the individual identifies and applies them to the sticker application area 20 of card 23 of FIG. 5B. The stickers applied are counted and entered in area 25. Indicia 21 and 22 identify the card as belonging to the Green category 22 and the personality style as the "The Logical Way." The reverse or second side of the sticker application card comprises information regarding the individual with this style.

FIG. 5C is an exemplar of information, which may be used to facilitate the use of the card. Quote area 30 illustrates an example of what the individual who identifies as Green, "The Logical Way" would feel about the workplace environment. An ideal environment description 33, describes the ideal work environment for the individual who identifies with the "The Logical Way" personality style. Strength area 35 illustrates the strengths that the individual who identifies with the "The Logical Way" personality style brings to the workplace environment.

Figure 6B:
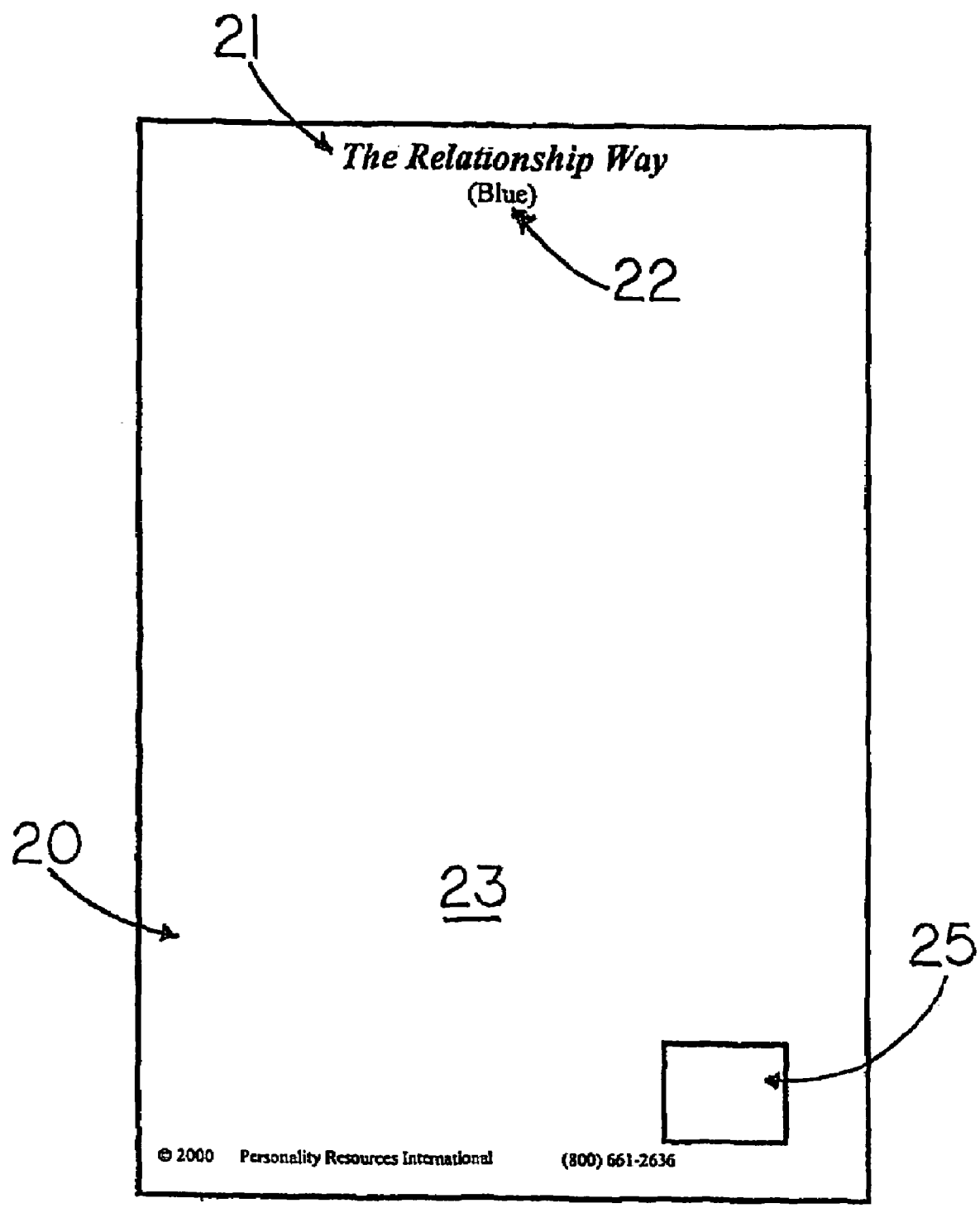
FIG. 6B is an illustration of "The Relationship Way" or Blue strip-sticker application card.

FIG. 6A illustrates the list of characteristics on the first peel-off sticker card that is the Blue, "The Relationship Way," card 13 with its list of characteristics 5. The individual selects the characteristics 5 with which the individual identifies and applies them to the sticker application area 20 of card 23 of FIG. 6B. The stickers applied are counted and entered in area 25. Indicia 21 and 22 identify the card as belonging to the Blue category 22 and the personality style as the "The Relationship Way." The reverse or second side of the sticker application card comprises information regarding the individual with this style.

FIG. 6C is an exemplar of information, which may be used to facilitate the use of the card. Quote area 30 illustrates an example of what the individual who identifies as Blue, "The Relationship Way," would feel about the workplace environment. An ideal environment description 33 describes the ideal work environment for the individual who identifies with the "The Relationship Way" personality style. Strength area 35 illustrates the strengths that the individual who identifies with the "The Relationship Way" personality style brings to the workplace environment.

The above terms to describe the "Ways" in indicia 22 are examples only. Other descriptions are deemed to be within the scope and spirit of the invention. For example, "The Relationship Way" may also be termed "The People-Centered Way."

Figure 7A:
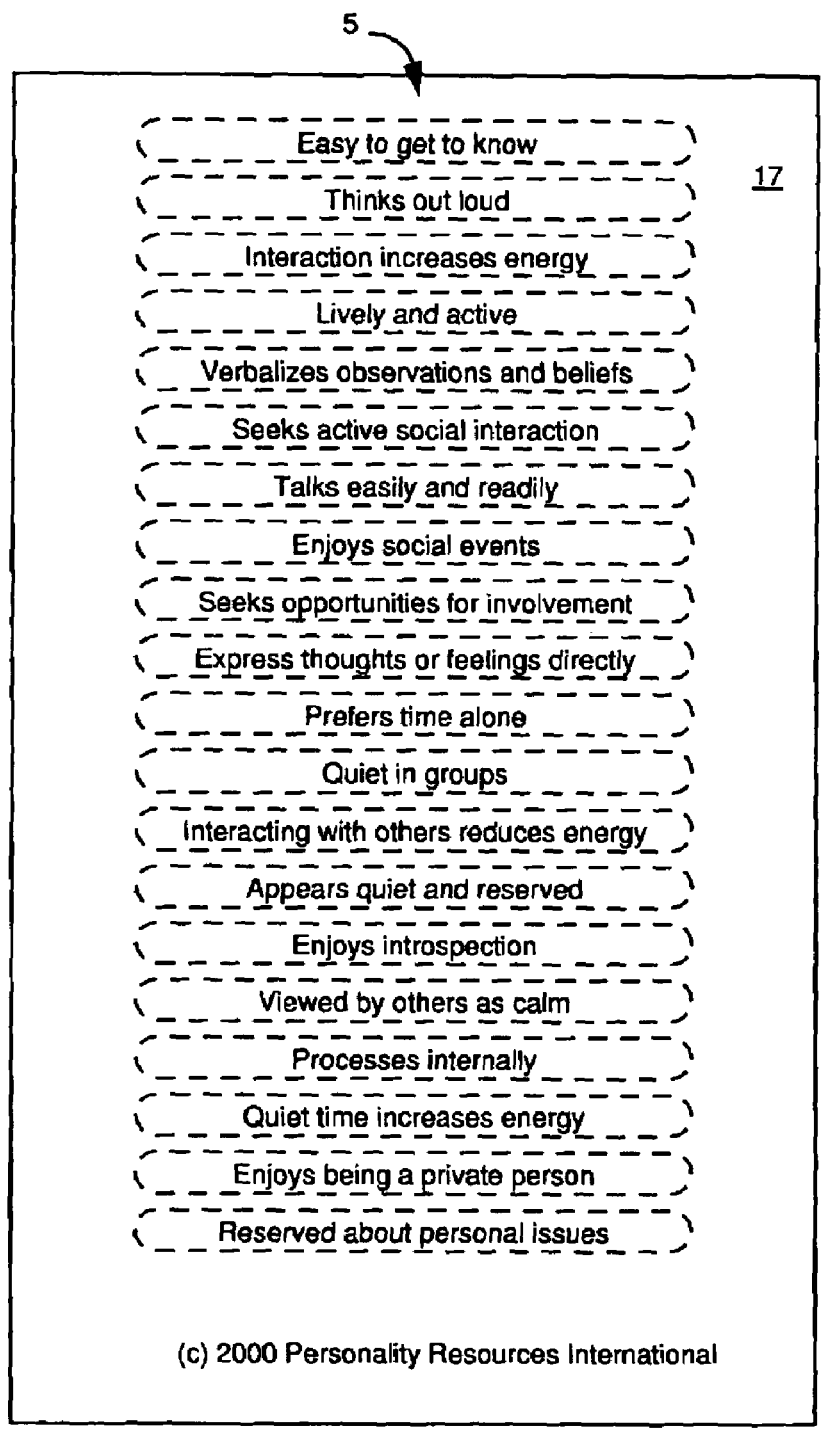
FIG. 7A is an illustration of the Extraversion vs. Introversion strip-sticker card.
Figure 7B:
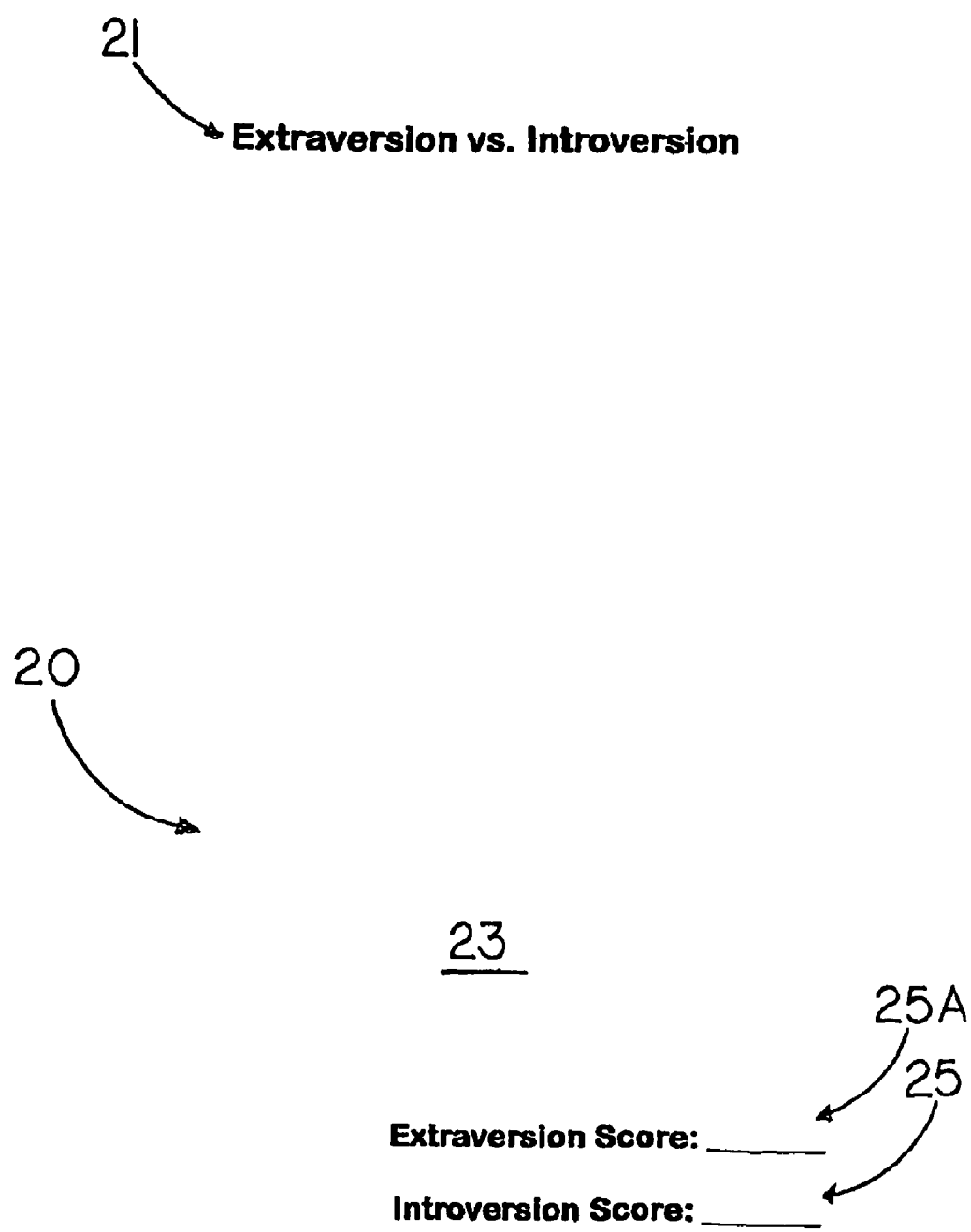
FIG. 7B is an illustration of the Extraversion vs. Introversion strip-sticker application card.

FIG. 7A illustrates the list of characteristics on the first peel-off sticker card, which is the Introversion versus Extraversion card 17 with its list of characteristics 5. Half of the characteristics on this card are identified with introversion and the other half of the characteristics identify with extraversion. The individual selects the characteristics 5 with which the individual identifies and applies them to the sticker application area 20 of card 23 of FIG. 7B. The stickers applied that identify with extraversion are counted to arrive at a first score. This score is entered into area 25a as the extraversion score. The stickers that identify with introversion are counted and entered in area 25b as an introversion score. Indicia 21 identify the card as the "Extraversion vs. Introversion." The reverse or second side of the sticker application card comprises information regarding extraversion and introversion.

FIG. 7C is an exemplar of information, which may be used to facilitate the use of the card. Area 73 illustrates the preferences of extraverts and area 75 illustrates the preferences of introverts.

As stated above, the cards may be used in association with a workbook in a team building and the like type meeting or seminar environment. FIG. 8 illustrates a profiling worksheet from the workbook. Sheet 800 comprises directions for completing the cards 810, a plurality of areas in which to list the scores 820, a plurality of areas which to place colored dots that correspond to the color of the primary, secondary, third and forth personality style 830. A set of Personality Style dots may be used to be place on the nametags of the meeting participants or on name plates in the meeting room. Other sets of Personality Style dots may be used throughout such a workbook.

Figure 9:
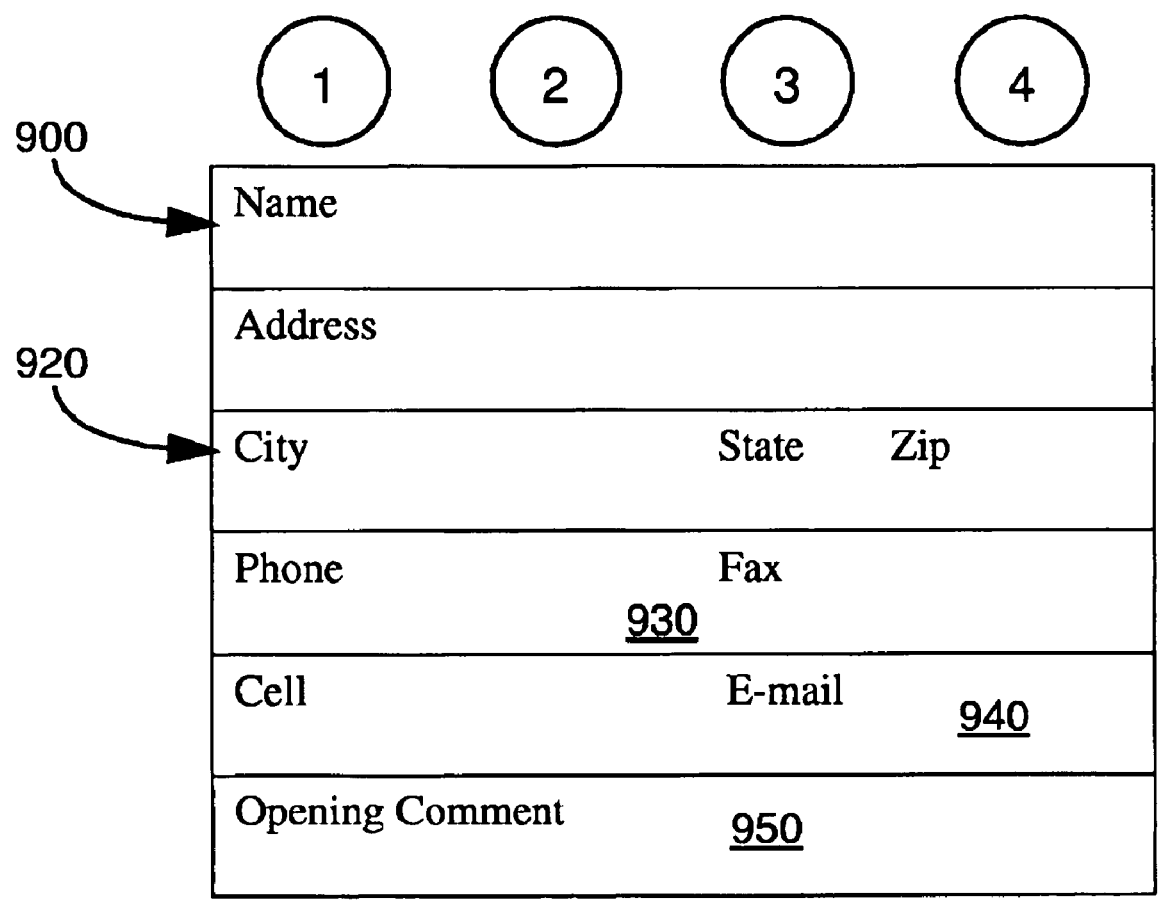
FIG. 9 is an illustration of a contact entry that utilizes knowledge of the contact's personality style.

The Personality Style Ways may also be used in the everyday business environments. FIG. 9 illustrates a typical contact card that may be used in connection with a rolodex or in a Personal Information Management (PIM) program. Contact card 900 comprises an area for color Personality style dots 910, address information area 920, phone/fax/cell number information area 930, e-mail information area 940, and opening comment area 950. The user may identify the personality style of the contact and create a phrase with which to open a conversation. If used in a PIM, e-mail editor of said PIM program may automatically insert the opening phrase when the user selects the contact to whom the e-mail is to be addressed.

Another example of the use of Personality Style ways is in project management programs. The creator of a new project worksheet may have a palette of available personal sorted by their Personality Style Ways. The user creator may create a team or ask a program agent to select a team based on their complementary personality styles (i.e. their strengths in regard to the project and the way their style my reinforce in order to achieve project success.

One advantage of the present invention over other types of personality analysis tools is the ability not only to determine dominate personality styles, but to score the relative strength of these personality styles. Prior Art systems such as the True Colors system only rank different personality styles in first, second, third, and fourth places. Thus, a participant may not have a true grasp of the relative strength of the different personality styles in his or her temperament. For example, if a user pulls 18 green strips, 12 orange strips and only one or two strips of blue and gold, the user will have a better grasp of their personality temperament and how to communicate as opposed to a ranking system which would provide only an ordering of Green/Orange/Blue/Gold. The scoring system tells the user that the green and orange personality styles are much more dominant that the blue and gold, in this example, and moreover, that the green and orange are relatively comparable in strength. An ordering system does not provide such information.

Although the present invention has been described in terms of specific embodiments and exemplars, it is anticipated that alterations and modifications thereof will no doubt become apparent to those skilled in the art. It is therefore intended that the following claims are interpreted as covering all such alterations and modification as falls within the true spirit and scope of the invention.

What is claimed is:

1. A method of personality testing, comprising the steps of:

providing, for at least one test subject, at least one pair of cards, each of the plurality of pairs of cards comprising a first card and a second card, the first card having a plurality of adhesive strips wherein each strip lists at least one personality characteristic, and the second card for applying selected strips from the first card, reviewing the personality characteristics on the adhesive strips on the first card and removing from the first card those adhesive strips corresponding to personality traits of the at least one test subject, attaching the adhesive strips removed from the first card to the second card, and tallying a number of adhesive strips attached to the second card to determine relative strength of a corresponding personality characteristic assigned to a pair of the at least one pair of cards.

2. The method of personality testing of claim 1, wherein the second card is provided with a first side for attaching selected adhesive strips from the first card, the second card being also provided with at least one score box for indicating a score, the second card also being provided with a second side with printed indicia indicating related personality and work characteristics for a selected pair of cards of the at least one pair of cards, said method further comprising the step of:

indicating a number of adhesive strips attached to the second card in the at least one score box as an indication of the relative strength of the corresponding personality characteristic.

3. The method of personality testing of claim 2, wherein the at least one pair of cards comprises a plurality of pairs of cards, each pair of the plurality of pairs of cards corresponding to a predetermined personality characteristic, said method further comprising the steps of:

determining the dominate personality trait of at least one test subject based upon the pair of cards among the plurality of pair of cards with the highest number of stickers tallied.

4. The method of claim 3, wherein the plurality of pairs of cards further include a pair of cards for determining relative introversion and extroversion of the at least one test subject, including a first card having a plurality of stickers in two groups representing introversion and extroversion characteristics, and a second card having two score boxes for introversion and extroversion characteristics, said method further comprising the step of:

tallying the number of introversion characteristic stickers applied to the second card and indicating an introversion score on one of the two score boxes, and tallying the number of extroversion characteristic stickers applied to the second card and indicating an extroversion score on the other of the two score boxes.

5. The method of claim 4, wherein the plurality of pairs of cards include a pair of cards predetermined to designate organizational skills.

6. The method of claim 4, wherein the plurality of pairs of cards include a pair of cards predetermined to designate action skills.

7. The method of claim 4, wherein the plurality of pairs of cards include a pair of cards predetermined to designate logical skills.

8. The method of claim 4, wherein the plurality of pairs of cards include a pair of cards predetermined to designate relationship skills.

9. The method of personality testing of claim 1, wherein the at least one pair of cards comprises a plurality of pairs of cards, each pair of the plurality of pairs of cards corresponding to a predetermined personality characteristic, said method further comprising the steps of:

determining the dominate personality trait of at least one test subject based upon the pair of cards among the plurality of pair of cards with the highest number of stickers tallied.

10. The method of claim 9, wherein the plurality of pairs of cards further include a pair of cards for determining relative introversion and extroversion of the at least one test subject, including a first card having a plurality of stickers in two groups representing introversion and extroversion characteristics, and a second card having two score boxes for introversion and extroversion characteristics, said method further comprising the step of:

allying the number of introversion characteristic stickers applied to the second card and indicating an introversion score on one of the two score boxes, and tallying the number of extroversion characteristic stickers applied to the second card and indicating an extroversion score on the other of the two score boxes.

11. The method of claim 10, wherein the plurality of pairs of cards include a pair of cards predetermined to designate organizational skills.

12. The method of claim 10, wherein the plurality of pairs of cards include a pair of cards predetermined to designate action skills.

13. The method of claim 10, wherein the plurality of pairs of cards include a pair of cards predetermined to designate logical skills.

14. The method of claim 10, wherein the plurality of pairs of cards include a pair of cards predetermined to designate relationship skills.

\* \* \* \* \*